United States Patent [19]

Zupancic et al.

[11] Patent Number: 5,114,741
[45] Date of Patent: May 19, 1992

[54] PHOTODEFINABLE INTERLEVEL DIELECTRICS

[75] Inventors: Joseph J. Zupancic, Bensenville, Ill.; Daniel C. Blazej, Annandale; Howard A. Fraenkel, Lebanon, both of N.J.

[73] Assignee: Allied-Signal Inc., Morris Township, Morris County, N.J.

[21] Appl. No.: 630,118

[22] Filed: Dec. 19, 1990

[51] Int. Cl.$^5$ ............................................... B05D 3/06
[52] U.S. Cl. .................................. 427/43.1; 156/655; 156/659.1; 156/662; 156/668; 456/904; 427/44; 522/166; 525/534; 528/154; 428/457
[58] Field of Search ................... 156/655, 659.1, 662, 156/668, 904; 427/43.1, 44; 428/457; 522/166; 525/534; 528/154

[56] References Cited

U.S. PATENT DOCUMENTS

| | | | |
|---|---|---|---|
| 4,816,498 | 3/1989 | Zupancic et al. | 522/166 |
| 4,824,920 | 4/1989 | Zupancic et al. | 525/534 |
| 4,908,096 | 3/1990 | Zupancic | 156/655 |

Primary Examiner—Michael Lusignan
Attorney, Agent, or Firm—Harold N. Wells; Gerhard H. Fuchs; Mary Jo Boldingh

[57] ABSTRACT

A predetermined pattern of a dielectric polymer is formed on a substrate from a mixture of prepolymers which are ethers of the reaction products of (a) a dicyclopentadiene and a phenol and (b) a dialdehyde and 3 to 4 moles of a phenol.

17 Claims, No Drawings

PHOTODEFINABLE INTERLEVEL DIELECTRICS

The U. S. Government has rights in this invention under U.S. Air Force Contract F336-15-89-C-5603.

PRIOR ART

This invention relates to materials used to provide isolation of conductive layers in microelectronic circuitry. In particular, it relates to polymeric materials which can be photopolymerized so that dielectric layers can be formed where desired in multilayer structures. Such layers must be excellent insulators, have good chemical resistance and, of course, must adhere to the substrate on which they are placed.

Polyimides have been used for such dielectrics since they have superior temperature and chemical resistance compared to many other polymers. Literature and patents disclosing of the use of polyimides are extensively discussed in U.S. Pat. No. 4,908,096 by one of the present inventors and incorporated herein by reference. The disadvantages of the polyimides are discussed, namely, that they release large amounts of volatiles during curing, absorb moisture, have poor adhesion, and have a relatively high coefficient of expansion. The patent discloses and claims the use of other polymers as interlevel dielectrics having improved properties, namely, vinyl benzyl or alkyl ethers of the condensation products of dialdehydes and phenols.

The present invention relates to other polymers which have been found to provide useful interlevel dielectrics.

In U.S. Pat. No. 4,824,920 one of the present inventors has disclosed thermosetting resins which are vinylbenzyl ethers of the reaction product of a dicyclopentadiene with a phenol and which have application to making laminated boards for electronic applications. The patent is incorporated by reference herein. In U.S. Pat. No. 4,816,498, incorporated by reference herein, another family of oligomeric condensation products was disclosed which differ from those just discussed in being the condensation products of dialdehydes with 3 to 4 moles of phenols. Such oligomers also are etherified to provide a mixture of vinylbenzyl and alkyl ethers. They may be used to make laminated boards for electronic applications. Such resins have been found to be useful as precursors for polymers for interlevel dielectrics, as will be seen in the discussion below.

SUMMARY OF THE INVENTION

This invention comprises a method of forming a predetermined pattern from a polymer on a substrate and the thus-created dielectric layers which may be used in an electronic interconnect structure.

Such patterns are created by coating onto the substrate a prepolymer and then irradiating the exposed portions of a masking pattern to render the prepolymer insoluble, then selectively dissolving the non-irradiated masked portions of the coating leaving the insoluble irradiated prepolymer, and curing the irradiated prepolymer to form an infusible glassy solid in the predetermined pattern.

The prepolymer is a mixture of two oligomers. One is a vinylbenzyl ether of the reaction product of a dicyclopentadiene with a phenol, the reaction product having the formula

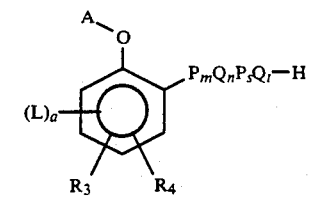

where

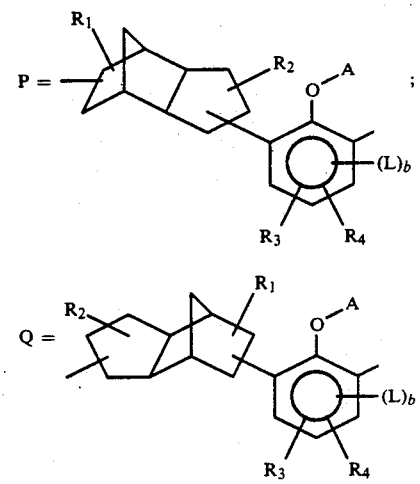

with
$R_1$, $R_2$ = H or alkyl of 1–10 carbon atoms;
$R_3$ = methyl;
$R_4$ = H;
A = H,

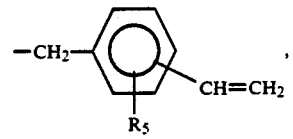

an alkyl moiety containing 1 to 10 carbon atoms, a cycloalkyl moiety having 5 to 10 carbon atoms, or benzyl, subject to the constraint that at least 50% of all A's are the vinyl benzyl moiety;
L = Br or Cl;
a = 0, 1, or 2;
b = 0 or 1;
m, n, s, and t are 0 or an integer, and $m+n+s+t=z$ is an integer from 1–10; and
$R_5$ = H, an alkyl moiety of 1–10 carbon atoms, a halogen or alkoxy moiety, or a monovalent aromatic radical. In a preferred embodiment, 70% of A's are vinyl benzyl and the remaining A's are propyl.

The second oligomer is an ether of the oligomeric condensation product of (a) 1 molar proportion of a dialdehyde and (b) from about 3 to about 4 molar proportions of a phenol; where the dialdehyde is selected from the group consisting of $OHC(CH_2)_nCHO$, where n = 0 or an integer from 1 to 6, cyclopentanedialdehyde, phthalaldehyde, isophthalaldehyde, terephthalaldehyde, hexahydrophthalaldehyde, cycloheptanedialdehyde, hexahydroisophthalaldehyde, hexahydroterephthalaldehyde, and cyclooctanedialdehyde; where the phenol has the structure $R_1C_6H_4OH$ and where $R_1$ is hydrogen or an alkyl group containing from 1 to about 10 carbon atoms; and where the phenol residue of said oligomeric condensation product is etherified with one or more substituents to afford ether moieties randomly selected from the group consisting of vinylbenzyl, alkyl moieties containing from 1 to 10 carbon atoms, cycloalkyl moieties from 5 to 10 carbon atoms, and benzyl, with the ratio of vinylbenzyl to other moieties being from 1:1 to about 6:1.

DESCRIPTION OF THE PREFERRED EMBODIMENTS

Polymeric Resins

In U.S. Pat. No. 4,824,920, one of the present inventors disclosed the preparation and use of ethers of the reaction product of a dicyclopentadiene with a phenol and their use in composites, especially laminated boards for electronic uses. It has now found that these compositions can be used as interlevel dielectrics, in combination with the oligomers of U.S. Pat. No. 4,816,498 where they have the advantages of low water absorption, low dielectric constant, low coefficient of thermal expansion, high glass transition temperature, high thermal stability, high solids coating concentrations, photochemical curability, thermal curability, and little or no volatiles generated during the cure process.

The prepolymers used in forming a pattern have the formula

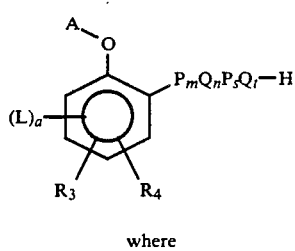

where

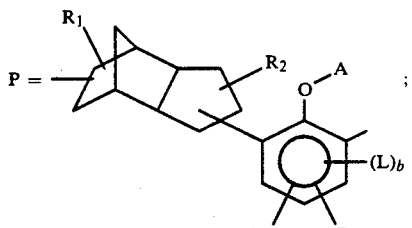

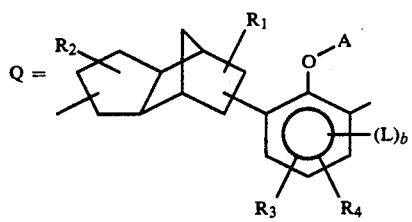

with
$R_1$, $R_2$ = H or alkyl of 1-10 carbon atoms;
$R_3$ = methyl;
$R_4$ = H;
$A$ = H,

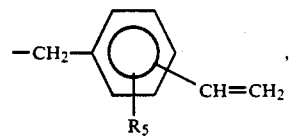

an alkyl moiety containing 1 to 10 carbon atoms, a cycloalkyl moiety having 5 to 10 carbon atoms, or benzyl, subject to the constraint that at least 50% of all A's are the vinyl benzyl moiety;
$L$ = Br or Cl;
$a$ = 0, 1, or 2;
$b$ = 0 or 1;
m, n, s, and t are 0 or an integer, and $m+n+s+t=z$ is an integer from 1-10; and
$R_5$ = H, an alkyl moiety of 1-10 carbon atoms, a halogen or alkoxy moiety, or a monovalent aromatic radical.

The dicyclopentadiene portion can be substituted in either ring. $R_1$ and $R_2$ usually are hydrogen, that is, an unsubstituted dicyclopentadiene is preferred in the practice of this invention but each of $R_1$ and $R_2$ can be an alkyl group, preferably a primary alkyl group, containing up to about 10 carbon atoms The lower alkyl groups, such as methyl, ethyl, propyl, and butyl, are especially preferred where the dicyclopentadiene is substituted. Substitution can be at any position of the dicyclopentadiene ring system but it is preferred that $R_1$ be at a carbon of the 5-member ring not bonded to the aryl group, and that $R_2$ is at the bridge or bridgehead carbon of the bicyclic ring portion.

The phenolic termini of our resins as well as the phenolic portion of p or Q may be substituted by a methyl group or a halogen atom. For the condensation with dicyclopentadiene mixtures of such phenols also may be used. The methyl group is at a position meta or para to the position bearing the oxygen atom. A para-substituted phenol is preferred in the practice of this invention because such a mixture tends to afford an amorphous resin, which is a beneficial feature, and is susceptible to photochemical curing.

The basic resins also can be readily modified to be flame retardant by incorporating halogen atoms into the aromatic rings Thus, L may be a halogen atom, especially bromine, and where the aromatic ring is halogenated a is 0, 1 or 2 and b is 0 or 1. Polyhalogenated materials are desired as flame retardants, which means that a and b are recommended to be maximized. Where the aromatic rings are not halogen substituted then both a and b are 0.

The fragments P and Q are subunits of the adduct. Where the adduct is an oligomer it may be a head-to-head, head-to-tail, or completely or partially random arrangement. Where oligomers are formed they are of relatively low molecular weight. The variables m, n, s, and t each are integers such that z, where z equals $m+n+S+t$, is an integer from 1 to 10, and usually is up to about 5, with z being 3 or 4 preferred in the practice of our invention.

The phenolic hydroxyls in the adduct are capped so as to be converted to ethers. At least 80% of the phenolic groups are so capped, and it is desirable that at least 90%, and even more desirable that at least 95%, of the phenolic groups are capped. Stated differently, in the formula above less than about 20% of the A moieties are hydrogen, and desirably less than 10%, even more desirably less than 5%, are hydrogen.

The best case results where the ether portion, A, is a vinylbenzyl moiety, that is, of the structure

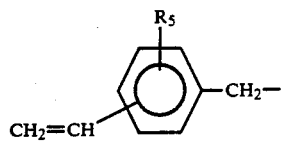

where the vinyl group is either meta or para to the CH$_2$, where R$_5$ is hydrogen, and which usually is a mixture of the meta- and para-isomers. R$_5$ is a chemically inert substituent selected from the group consisting of hydrogen, alkyl moieties containing from 1 to about 10 carbon atoms, the halogens, alkoxy moieties containing from 1 to about 10 carbon atoms, and monovalent radicals whose parent is an aromatic hydrocarbon.

However desirable it may be to have all the phenolic hydroxyls end-capped with vinylbenzyl moieties, there is a decided cost advantage when fewer than all of the other groups are vinylbenzyl usually at the expense of a somewhat lower dielectric constant. In our invention it is required that at least 50% of the A moieties different from hydrogen be a vinylbenzyl moiety, but a product with better performance characteristics results when from 70 to 100% of the ether groups are vinylbenzyl, and the best product results when 95 to 100% of such groups are vinylbenzyl. In many applications less than complete end-capping with vinyl benzyl groups is acceptable, but all of the hydroxyl groups should be capped.

In those cases where less than all of the ether groups are vinylbenzyl, then we are partial to resins where A is an alkyl group containing from 1 to 10 carbons, a cycloalkyl group having 5 to 10 carbons, or a benzyl group. Where A is an alkyl group, the primary alkyl groups are given priority, especially the primary lower alkyl groups containing from 1 to 4 carbon atoms. Thus, the most desirable alkyl groups consist of methyl, ethyl, 1-propyl, 1-butyl, and 2-methyl-1-propyl. Other alkyl groups are represented by 1-pentyl, 1-hexyl, 1-heptyl, 1-octyl, 1-nonyl, 1-decyl, 2-methyl-1-butyl, 3-methyl-1-butyl, 2,3-dimethyl-1-butyl, 3,3-dimethyl-1-butyl, 2-methyl-1-pentyl, and so forth. However, it is to be emphasized that a benzyl group also operates quite satisfactorily in the practice of our invention. The most common cycloalkyl groups used in our invention are 5- and 6-membered cycloalkanes, unsubstituted or alkyl substituted so as to contain 5 to 10 carbon atoms. Examples are cyclopentyl, cyclohexyl, methylcyclopentyl, dimethylcyclopentyl, ethyl cyclopentyl, propylcyclopentyl, butylcyclopentyl, pentylcyclopentyl, ethylmethylcyclopentyl, methylpropylcyclopentyl, butylmethylcyclopentyl, methylcyclohexyl, dimethylcyclohexyl, ethylcyclohexyl, propylcyclohexyl, butylcyclohexyl, and so forth. The 1-propyl group is an especially desirable alternative to the vinylbenzyl moiety, and resins where less than 5% of the A groups are hydrogen with the remainder being vinylbenzyl or 1-propyl in a ratio from 1.1:1 to about 6:1 are highly recommended. In a preferred embodiment, A is at least 70% vinyl benzyl and the remaining A's are propyls.

The use of a mixture tends to promote formation of an amorphous resin which is desirable both in increasing the solubility of the resin in a solution, in promoting good film-forming qualities, and in providing a stable, non-flaking coating. A desirable mixture of resins is one which consists of from about 5 to about 20% by weight of a resin where z=1, about 10 to about 30% with z=2, about 5 to about 30% with z=3, about 5 to about 30% with z=4, and about 5 to about 30% with z=5-10.

The appended vinyl groups are readily crosslinked in a curing step effected by thermal, chemical, or radiative means. Thermal curing is generally done in the temperature range between about 100° and about 300° C., and in practice at a temperature between about 150° and about 200° C. for 0.5-5 hours with post curing at about 180°-300° C. for about 0.5-24 hours. Curing also may be brought about using a free radical initiator, such as azo-bis-isobutylronitrile, benzoyl peroxide, di-t-butyl peroxide, etc. Curing may be effected as well as irradiation, especially by visible and ultraviolet light in the presence of a suitable photoinitiator or sensitizer. Whether thermal, chemical, or photochemical curing is performed, the resin becomes extensively crosslinked and sets to an infusible, insoluble glassy solid.

The resins of this invention may be prepared by any convenient method known in the art. However, they are most readily prepared by reacting a vinylbenzyl halide with the dicyclopentadiene-phenol adduct in a basic solution. Generally a mixture of the meta- and para-isomers of vinylbenzyl chloride are used, although the bromide and, to a lesser extent, the iodide also may be used. The reaction may be conveniently performed in an alcoholic potassium hydroxide solution, often containing acetone, N-methylpyrrolidone, or some other organic cosolvent, at the reflux temperature. Where some of A are alkyl, cycloalkyl, or benzyl moieties these may be prepared by reacting a suitable alkyl, cycloalkyl, or benzyl halide with a partially vinylbenzyl end-capped adduct, or by reacting the uncapped adduct with a mixture of halides.

The second type of oligomers are ethers of oligomeric condensation products of 1 molar proportion of certain dialdehydes with from about 3 to about 4 molar proportions of a phenol. More particularly, the ether moiety is randomly selected from among the vinylbenzyl moiety, alkyl moieties containing from 1 to 10 carbon atoms, cycloalkyl moieties having from 5 to about 10 carbon atoms, and the benzyl moiety, where the ratio of the vinylbenzyl to other ether moieties is at least 1:1 and may be as great as 6:1.

The phenolic oligomers are the condensation products of 1 molar proportions of selected dialdehydes with 3 to 4 molar proportions of a phenol. Although more than 4 molar proportions of a phenol can be used in the practice of this invention, no more than 4 molar proportions will react with the dialdehydes.

One class of dialdehydes which may be used in this invention are the linear, terminal alkylene dialdehydes of formula OHC(CH$_2$)$_r$CHO where r is 0 or an integer from 1 to 6. Such dialdehydes include glyoxal, malondialdehyde, succinidialdehyde, glutaraldehyde, adiphaldehyde, pimelaldehyde, and sebacaldehyde. Those aldehydes where n is 0–4 are particularly preferred, and glyoxal (n=0) is especially favored in the practice of this invention.

Other aldehydes which may be employed in preparation of the oligomeric condensation products include cyclopentanedialdehyde, phthalaldehyde, isophthaldehyde, terephthalaldehyde, the hexahydrophthalaldehydes (i.e., the reduced counterpart of the phthalaldehydes where the aromatic ring has been reduced to a cyclohexane ring), cycloheptanedialdehyde, and cyclooctanedialdehyde.

The oligomers are the condensation product of 1 molar proportion of the aforementioned dialdehydes with from 3 to about 4 molar proportions of a phenol. The phenol has the general structure $R_6C_6H_4OH$ where $R_6$ is hydrogen or an alkyl group containing from 1 through about 8 carbon atoms. The most desirable phenol is phenol itself, that is, the case where $R_6$ is hydrogen. Where $R_6$ is an alkyl group it is most desirable that the alkyl group contain from 1 to about 4 carbon atoms, and cresol, the case where $R_6$ is a methyl group is another preferred species of phenol.

The condensation product is analogous to phenol-formaldehyde resins. That is, the products result from the condensation of 2 molar proportions of a phenol with each aldehyde group. In the simplest case, which can be looked as the "monomeric" product, using phenol and glyoxal to exemplify the reaction, the product has the structure

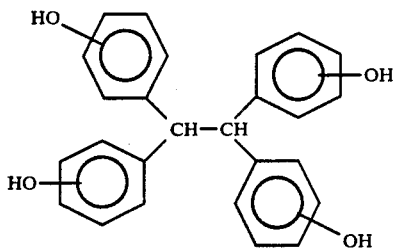

where the hydroxyls are almost exclusively ortho and para, and largely para, to the point of condensation of the phenol and glyoxal. However, the product above has 4 phenolic groups per molecule, and any one of these may react with another molecule of glyoxal which then further condenses with three other molecules of phenol to give the structure

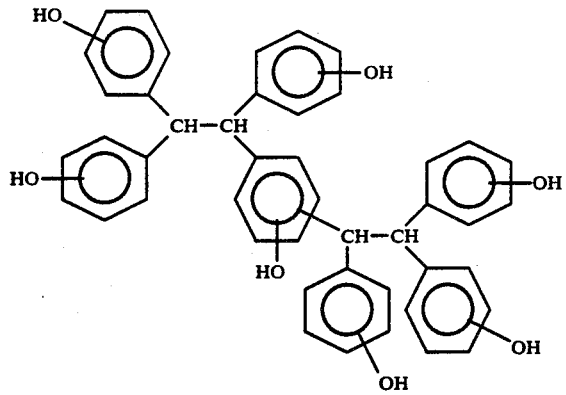

The oligomeric product above results from a molar preparation of 7 phenols to 2 glyoxals. This oligomer in turn can react with another molecule of glyoxal and the latter can react further with 3 additional phenols to give the next higher oligomer of the structure

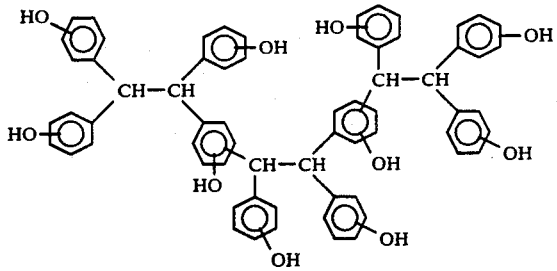

which has the molar ratio of 10 phenolic groups to 3 glyoxals. In a similar fashion, the next higher oligomer has a molar ratio of phenol to glyoxal of 13:4, the next higher of 16:5, and so forth, with the limiting molar ratio being 3:1. It needs to be maintained that a ratio less than 3:1 will never be achieved without internal cyclization, i.e., one molecule of glyoxal is required to react with at least 2 phenolic moieties of the oligomer. In a similar fashion, the condensation product which is the "monomer" has a limiting ratio of phenol-glyoxal of 4:1.

The condensation products are themselves phenols, as mentioned above, and are a mixture of oligomers. This mixture can be characterized by the number of phenolic moieties per molecule. We are concerned with those condensation products which have from 4 to about 60 phenolic moieties per molecule, and more usually between four and about 22 phenolic moieties per molecule. The product being a mixture of oligomers, the preferred mixture is characterized by having as an average between about 5 and about 8 phenolic moieties per molecule.

More specifically, where the dialdehyde is glyoxal and the phenol is phenol itself each oligomeric product has a molecular weight between about 400 and 6000, and more desirably between about 400 and about 2200. The mixture of oligomeric products may be characterized by an average molecular weight of between about 500 and about 800.

The interlevel dielectric resins of this invention are ethers of the aforedescribed oligomeric condensation products. In one variant of our invention the phenolic condensation products are halogenated prior to ether formation in order to make the final resins more flame retardant. Increased flame retardancy occurs especially when the halogen is chlorine or bromine, and the use of a brominated product is preferred. The halogen is introduced into positions ortho and para to the phenolic hydroxyl group. If all of the ortho and para positions are available a maximum of three halogen atoms per phenolic moiety may be introduced. Often it is desirable to prepare the maximally halogenated oligomeric condensation product, although at times a halogen content less than the maximum is advantageous. However, in the latter variant it should be clear that there is at least one chlorine or bromine atom per phenolic moiety. The phenolic condensation products are capped so as to convert substantially all (greater than about 99.5%) of the hydroxyls to ether moieties. Each of the ether moieties is randomly selected from the group consisting of vinylbenzyl, alkyl containing 1 to 10 carbon atoms, cycloalkyl of from 5 to 10 carbon atoms, and benzyl moieties as described above with respect to the first type of oligomer where the ratio of the vinylbenzyl to all other ether moieties is at least 1:1 and may be as high as 6:1.

The prepolymers may be prepared by acid catalyzed condensation of phenols with dialdehydes followed by end-capping substantially all the phenolic hydroxyls by converting them to ethers. Acid catalyzed condensation is preferred to avoid the formation of terminal hydroxyl methylene groups, —CH$_2$OH. End-capping by ether formation can be effected by any suitable means, such as by reacting the phenolic condensation product with an alkyl or benzyl halide in a basic medium.

The resulting interlevel dielectric oligomers may be polymerized with attendant crosslinking by a variety of curing means. When curing is effected by thermal means, it generally is autoinitiated by heating the oligomer resin in air at a temperature between about 100° and 300° C., and more particularly between about 120° and 200° C. Curing also may be brought about by chemical means using a free radical initiator such as azo-bis-isobutyronitrile, benzoyl peroxide, di-t-butyl peroxide, etc. In the present invention curing is begun by irradiation, especially by visible and ultraviolet light in the presence or absence of a suitable photoinitiator or sensitizer, followed by thermal curing to produce an infusible, insoluble glassy solid.

Photodefinable Applications

The oligomers may be used as a passivant, as an interlevel dielectric, as a means of providing device deep dielectric isolation (insulator isolating trenches), as a high temperature solder mask, a photoresist, etc. Although much of what follows describes its use primarily as an interlevel dielectric, the skilled worker will recognize from this description how to use the materials of this invention in other applications as well.

The oligomers are applied as a coating to a suitable substrate. For the most part the substrates used will be a silicon wafer, a silicon chip of an integrated circuit, a printed circuit board or a ceramic substrate. The photosensitive oligomers may be applied by spin coating, spray coating, by use of a doctor knife, or any other conventional techniques known in the art to obtain a uniform coating. Where the viscosity is too high, a solution of the resin in a suitable solvent may be used. The oligomers are soluble in a broad class of solvents including polar aprotic solvents, aromatic hydrocarbons, halogenated hydrocarbons, ketones, ester, and so forth. Examples of solvent which may be employed in the practice of our invention include dimethylformamide (DMF), hexamethylphosphoramide (HMPA), N-methylacetamide (NMAc), dimethylsulfoxide (DMSO), N-methylpyrrolidone (NMP), benzene, toluene, xylene, dichloromethane, chloroform, carbon tetrachloride, chlorobenzene, tetrachloroethane, tetrachloroethylene, trichloroethane, gamma-butyrolactone, methyl ethyl ketone, diethyl ketone, hexanone, heptanone, octanone, methyl acetate, ethyl acetate, methoxy ethanol, ethoxy ethanol, and so forth. The solvent should be unreactive with both the substrate and the photosensitive oligomers and able to dissolve the resins to provide at least about a 10 weight-volume percent solution. Since the solvent is typically removed prior to further processing, it is also preferable that as low boiling a solvent as possible be used consistent with the foregoing considerations.

Although the oligomers may be photopolymerized directly, a photosensitizer or photoinitiator may be used and may be useful to decrease irradiation time. Where a photosensitizer or photoinitiator is used it will be added with the oligomers at the coating stage and will be present in an amount from about 0.001 to about 5.0 weight percent relative to the oligomerics. Examples of photosensitizers or photoinitiators which may be successively used in the practice of this invention include such materials as benzophenone, 4,4'-bis(dimethylamino)benzophenone, xanthone, acetophenone, 4-trifluoromethyl-acetophenone, triphenylene, thioxanthone, anthraquinone, 4-phenylbenzophenone, naphthalene, 2-acetonaphthalene, 1-acetonaphthalene, chrysene, anthracene, 9,10-dichloroanthracene, pyrene, triphenylene, 1-fluoronaphthalene, 1-chloronaphthalene, 1-bromonaphthalene, 1-iodonaphthalene, 1,3-dicyanobenzene, dimethyl isophthalate, diethyl isophthalate, methyl 3-cyano-benzoate, ethyl 3-cyanobenzoate, phenyl 3-cyano-benzoate, 2,2-dimethoxyacetophenone, 2,2-diethoxyacetophenone, 2,2'-dimethoxy-2-phenylacetophenone, 2,2'-diethoxy-2-phenylacetophenone, benzoin methyl ether, and 1-phenyl-1,2-propanedione-2-O-benzoyloxime. Preferred sensitizers include benzophenone, 4,4'-bis(dimethylamino)benzophenone, 1,3-dicyanobenzene, dimethyl isophthalate, diethyl isophahalate, methyl 3-cyano-benzoate, and phenyl 3-cyano-benzoate.

Where the photosensitive oligomers have been applied as a solution to the substrate the solvent used must be removed prior to irradiation. Consequently, it is conventional to heat the coated substrate for a time sufficient to remove essentially all of the solvent present, if any, prior to irradiation, a stage known as the "softbake." It is for this reason that the use of a low boiling solvent is preferred. It is acceptable to use enough heat to provide a semicured coating, especially since the oligomers may begin to cure at temperatures as low as about 110° C. The softbake can be carried out in vacuum, under an inert atmosphere (e.g., nitrogen, helium, argon, etc.) or in air.

A mask containing the desired pattern or image is placed on or adjacent to the coated substrate and the oligomeric coating is then irradiated through the mask by x-ray, electron beam, ion beam, ultraviolet, or visible radiation. For reasons of economy and ease of fabrication it is preferred to use radiation in the range from about 200 to about 800 nanometers. Since lower wave length radiation tends to afford better resolution, irradiation in the 200-500 nm range is preferred. With this treatment the irradiated portion of the coating becomes crosslinked so that the photocrosslinked oligomer is rather insoluble in the same solvent in which the original photosensitive oligomers remain quite soluble.

Irradiation may be done in either the presence or absence of oxygen. Exposure time necessary for adequate photocrosslinking to afford the differential solubility characteristic sought depends upon the wavelength of the light used, its intensity, the presence or absence of a photosensitizer or photoinitiator, and so forth, with a variation from a few seconds up through several minutes. For production purposes the shorter exposure times are highly preferred. One desirable characteristic of the photosensitive oligomers of this invention is that they photochemically crosslink throughout the thickness of the film, and therefore the pattern shows minimal undercutting upon development.

The selective pattern appears upon development with the solvent. As mentioned above, upon irradiation the photosensitive oligomeric resin becomes extensively crosslinked with a subsequent large differential solubility between the crosslinked, or irradiated, and non-crosslinked, or non-irradiated, portions of the oligomers. The solvents used in the development are in general the same ones used in preparing a solution of the oligomers for coating purposes. Thus, classes of solvents include aprotic solvents, aromatic hydrocarbons, halogenated hydrocarbons, ketones, esters, the Carbitols, and mixtures thereof.

Upon development selective patterns appear where the elevated portions correspond to the photochemically crosslinked oligomers. These relief structures are then thermally cured to afford a highly crosslinked, infusible, glassy solid highly resistant to elevated temperatures, chemical degradation, ion transport, and which serves as an effective protective layer and dielectric insulator. Curing is attended by crosslinking of the vinyl groups and may be effected either thermally, chemically, or photochemically, with thermal curing preferred. Thermal curing is generally done in the temperature range between about 100° C. and about 300° C., and often is done in stages. So, for example, curing may first be effected at a temperature postcuring at about 180° C.-300° C. for about 0.5-24 hours. Curing also may be brought about using a free radical initiator, such as azo-bis-isobutyronitrile, benzoyl peroxide, di-t-butylperoxide, and so on.

The oligomers of the invention have been found particularly useful in photodefinable applications since they may be coated as solutions with high solids levels and thus less solvent must be evaporated. Also, since no volatile by-products are generated during curing the shrinkage of the films is minimized.

MULTILAYER PROCESSING

The substrate (i.e., ceramic, alumina, silicon, printed wiring board, etc.) may be cleaned with conventional cleaning solvents (e.g., methylene chloride, chloroform, Genesolv ®, trichloroethylene, ethanol, methanol, sodium bisulfite, sodium sulfite, potassium sulfite, etc.) employing normal cleaning processes as known in the art. In addition, the substrate may contain circuitry already deposited upon it. The substrate may be utilized after the cleaning process or may be surface treated to promote adhesion between the substrate and the metals and/or polymer dielectric layer.

If used, an adhesion promoter between the substrate and the dielectric layer may be chosen from a range of surface silylating agents containing reactive groups capable of reacting with the polymers of the invention. Examples of surface silylating agents which can be employed are: vinylmethyldimethoxysilane, vinyltrimethoxysilane, vinylmethyldiethoxysilane, vinyltriethoxysilane, diethoxymethylvinylphenethylsilane, dimethoxymethylvinylphenethylsilane, triethoxyvinylphenethylsilane, trimethoxyvinylphenethylsilane, etc. Preferred silylating agents are vinylmethyldimethoxysilane, vinylmethyldiethoxysilane, diethoxymethylvinylphenethylsilane, and dimethoxymethylvinylphenethylsilane. The surface silylating agent would be applied to the substrate via dipping, spin coating, or other techniques from an alcohol-water solution. For example, a 1 to 10 wt. % solution of the silylating agent is dissolved in 85 to 98 wt. % of alcohol (e.g., methanol, ethanol, isopropanol, etc.) and 1 to 13 wt. % of water. The substrate is dipped in this solution for 15 seconds to 5 minutes, air dried for 1 minute to 5 hours, and then soft baked for 1 minute to 5 hours at 60° to 100° C. either in a convection oven, vacuum oven or hot plate.

The cleaned and/or surface treated substrate will be covered with a metal pattern before being covered with the dielectric layer of the invention. For example, a 500 to 1000Å layer of chromium, 8000 to 20000Å layer of copper and a 500 to 1000Å layer of chromium may be sputtered onto the surface. Then, the metal layer is coated with a commercial photoresist and processed according to the recommended processing scheme utilizing a spin coat, soft bake, imaging, developing, and hard bake cycle. This exposes portions of the metal layer to be removed by etching to create the pattern. The metals are etched utilizing standard wet techniques, for example: The top chromium layer is etched with a 1 to 30 hydrochloric acid solution activated with aluminum for 10 seconds to 5 minutes; the copper layer is etched with a sodium persulfate solution for 10 seconds to 10 minutes; the bottom chromium layer is etched with a 1 to 30% hydrochloric acid solution activated with aluminum for 10 seconds to 5 minutes; and finally the etched substrate is washed with deionized water for 10 to 60 seconds. Then the remaining photoresist is stripped from the metal pattern as per the processing technique recommended for the photoresist. Finally the cleaned substrate is dried prior to the next processing step.

The dielectric layer is coated onto the substrate and its metal pattern and processed as follows: The prepolymer (e.g., 10 to 80 wt. %) solution in an appropriate solvent (toluene, NMP, DMF, etc.) is spin coated onto the substrate at a speed of 500 to 2500 rpm for 30 to 90 seconds; the prepolymer coated substrate is soft baked at a temperature of 25° to 60° C. for 15 minutes to 24 hours in a vacuum oven with or without a nitrogen bleed; the soft-baked coating is then imaged with a UV light source (220-320 nm range) for 15 seconds to 30 minutes employing a mask of desired design for vias and the like; the photocured polymer is then developed with an appropriate solvent system (e.g., toluene, toluene/hexane, toluene/ethanol, cyclohexane, etc.) at 25° to 35° C. with or without ultrasonics or via spraying for 15 to 120 seconds; the developed substrate can then be exposed to a stop or rinse bath or solvent spray based upon a solvent system miscible with the developing solvent but a poor solvent for the polymer system (for example hexane, pentane, ethanol, etc.) (optional step); the vias are then cleaned with a plasma or wet etch; and finally the dried substrate is hard baked in vacuum or under an inert atmosphere (nitrogen, argon, etc.) with a cure cycle including a ramp from 252 to 300° C. for 30 minutes to 2 hours, a hold at 300° C. for 1 hour and then a cool down from 300 to 25° C. with a 30 minute to 3 hour ramp.

The process is repeated as required in order to form an electronic interconnect structure of desired electrical and dielectric levels.

EXAMPLE 1

Synthesis of Styrene Terminated Para-Cresol Dicyclopentadiene (STPCDP (70VBz/30Pr))

200.0 grams of the para-cresol dicyclopentadiene (PCDP) from Borden Chemical (Mn=520, Mw=1100, dispersity of 2.12) was dissolved in 700 mL of N-methylpyrrolidinone (NMP) in a 2000 mL 3-neck round bottom flask equipped with mechanical stirrer, addition funnel, condenser, thermometer, nitrogen purge and Therm-O-Watch. To this reaction mixture was added 123.06 g (0.806 moles) of vinylbenzylchloride (60/40 para/meta isomer ratio) and 0.30 g of 2,6-di-tert-butyl-p-cresol (BHT). The reaction mixture was heated to 60° C. and 52.78 g (0.941 moles) of potassium hydroxide in 125 mL of methanol was added dropwise over a 30 minute interval. The reaction was maintained at 60° C. for 16 hrs with stirring under a nitrogen purge. To this reaction mixture was added 31.32 g (0.254 moles) of npropylbromide and then 15.34 g (0.273 moles) of potassium hydroxide in 80 mL of methanol over a 1 hr. interval. The reaction was maintained at 60° C. for 3.5 hours and then allowed to cool to room temperature. The reaction mixture was then transferred to a separatory funnel, and 2.0 Liters of toluene added and then washed thrice with 1.0 Liters of water, dried over magnesium sulfate, filtered and concentrated under vacuum, yielding a red resinous product; $Mn = 630$, $Mw = 1200$, dispersity of 1.9.

EXAMPLE 2

Synthesis of Styrene Terminated Para-Cresol Dicyclopentadiene (STPCDP (70VBz/30Pr))

500.0 grams of the para-cresol dicyclopentadiene (PCDP) from Borden Chemical ($Mn = 520$, $Mw = 1100$, dispersity of 2.12) was dissolved in 1750 mL of N-methylpyrrolidinone (NMP) in a 5000 mL 3-neck round bottom flask equipped with mechanical stirrer, addition funnel, condenser, thermometer, nitrogen purge and Therm-O-Watch. To this reaction mixture was added 307.65 g (2.016 moles) of vinylbenzylchloride (60/40 para/meta isomer ratio) and 1.43 g of 2,6-di-tert-butyl-p-cresol (BHT). The reaction mixture was heated to 60° C. and 131.95 g (2.35 moles) of potassium hydroxide in 312 mL of methanol was added dropwise over a 6.0 hrs. interval. The reaction was maintained at 60° C. for 16 hrs. with stirring under a nitrogen purge. To this reaction mixture was added 78.30 g (0.637 moles) of npropylbromide, and then added 38.35 g (0.630 moles) of potassium hydroxide in 200 mL of methanol over a 20 minute interval. The reaction was maintained at 60° C. for 3.5 hours and then allowed to cool to room temperature. The reaction mixture was then transferred to a separatory funnel, and 2.0 Liters of toluene added and then washed with 2.0 Liters of water, once with saturated sodium chloride solution, and finally washed with a saturated ammonium chloride solution, dried over magnesium sulfate, filtered and concentrated under vacuum, yielding a red resinous product; $Mn = 500$, $Mw = 960$, dispersity 1.9.

EXAMPLE 3

Synthesis of Styrene Terminated Para-Cresol Dicyclopentadiene (STPCDP (70VBz/30Pr))

324.0 grams (2.996 moles) of para-cresol was charged into a 1000 mL 3-neck round bottom flask equipped with mechanical stirrer, addition funnel, condenser, thermometer, Therm-O-Watch, and Nitrogen purge. The reaction flask is heated to 90° C. under nitrogen with stirring. To the melted p-cresol is added 6.0 mL (0.041 moles) of boron trifluoride etherate. To this reaction mixture was added 262.0 g (1.982 moles) of dicyclopentadiene over a 2.2 hour interval, the reaction was maintained at 90° C. for 1 hour with stirring; then the unreacted p-cresol was vacuum distilled from the reaction mixture. The para-cresol dicyclopentadiene (PCDP) resin was isolated by pouring into a stainless steel pan and allowing to cool to ambient temperature; $Mn = 650$, $Mw = 1500$, dispersity of 2.31.

207.2 grams of the para-cresol dicyclopentadiene (PCDP) from above was dissolved in 700 mL of N-methylpyrrolidinone (NMP) in a 2000 mL 3-neck round bottom flask equipped with mechanical stirrer, addition funnel, condenser, thermometer, nitrogen purge and Therm-O-Watch. To this reaction mixture was added 127.5 g (0.835 moles) of vinylbenzylchloride (60/40 para/meta isomer ratio) and 0.20 g of 2,6-di-tert-butyl-p-cresol (BHT). The reaction mixture was heated to 60° C. and 54.68 g (0.975 moles) of potassium hydroxide in 130 mL of methanol was added dropwise over a 2.0 hours interval. The reaction was maintained at 60° C. for 16 hrs with stirring under a nitrogen purge. To this reaction mixture was added 32.45 g (0.263 moles) of n-o propylbromide, and then added 15.89 g (0.283 moles) of potassium hydroxide in 80 mL of methanol over an 1.33 hour interval. The reaction was maintained at 60° C. for 8 hours and then allowed to cool to room temperature. The reaction mixture was then transferred to a separatory funnel, and 1.5 Liters of toluene added and then washed thrice with 2.0 Liters of water, dried over magnesium sulfate, filtered and concentrated under vacuum, yielding a red resinous product; $Mn = 770$, $Mw = 1400$, dispersity of 1.82.

EXAMPLE 4

Synthesis of Styrene Terminated Para-Cresol Dicyclopentadiene (STPCDP (70VBz/30Pr))

500.0 grams of para-cresol dicyclopentadiene (PCDP) from Borden Chemical ($Mn$ 520, $Mw$ 1100, dispersity of 2.12) and 420 mL of ortho-dichlorobenzene was charged into a 2000 mL 3-neck round bottom flask equipped with mechanical stirrer, addition funnel, condenser, thermometer, Therm-O-Watch, and Nitrogen purge. The reaction mixture was heated to 60° C. under nitrogen with stirring; after complete dissolution of PCDP then 6.0 mL (0.041 moles) of boron trifluoride etherate was added. To this reaction mixture was added 71.12 g (0.538 moles) of dicyclopentadiene over a 1.1 hour interval, the reaction was maintained at 60° C. with stirring during the addition; then the reaction was heated to 150° C. for 4 hours. The ortho-dichlorobenzene and unreacted dicyclopentadiene was vacuum distilled from the reaction mixture. The para-cresol dicyclopentadiene (PCDP) resin was isolated by pouring into a stainless steel pan and allowing to cool to ambient temperature, yield 332.0 g; $Mn = 800$, $Mw = 2500$, dispersity of 3.12.

318.5 grams of the para-cresol icyclopentadiene (PCDP) from above was dissolved in 1100 mL of N-methylpyrrolidinone (NMP) in a 2000 mL 3-neck round bottom flask equipped with mechanical stirrer, addition funnel, condenser, thermometer, nitrogen purge and Therm-O-Watch. To this reaction mixture was added 195.0 g (1.278 moles) of vinylbenzylchloride (60/40 para/meta isomer ratio) and 0.30 g of 2,6-di-tert-butyl-p-cresol (BHT). The reaction mixture was heated to 60° C. and 84.05 g (1.498 moles) of potassium hydroxide in 200 mL of methanol was added dropwise over a 3 hour interval. The reaction was maintained at 60° C. for 16 hrs with stirring under a nitrogen purge. To this reaction mixture was added 49.88 g (0.406 moles) of n-propylbromide, and then 24.43 g (0.435 moles) of potassium hydroxide in 125 mL of methanol added over a 2 hour interval. The reaction was maintained at 60° C. for 4 hours and then allowed to cool to room temperature. The reaction mixture was then transferred to a separatory funnel, and 1.5 Liters of toluene added and then washed once with 4 Liters of water and twice with saturated sodium chloride solution, dried over magnesium sulfate, filtered and concentrated under vacuum, yielding a red resinous product; Mn=700, Mw=1600, dispersity of 2.3.

EXAMPLE 5

Synthesis of Styrene Terminated Para-Cresol Dicyclopentadiene (STPCDP (70VBz/30Pr))

324.0 grams (2.996 moles) of para-cresol was charged into a 1000 mL 4-neck resin kettle equipped with mechanical stirrer, addition funnel, condenser, thermometer, Therm-O-Watch, and Nitrogen purge. The reaction flask is heated to 90° C. under nitrogen with stirring. To the melted p-cresol is added 6.0 mL (0.041 moles) of boron trifluoride etherate. To this reaction mixture was added 288.2 g (2.180 moles) of dicyclopentadiene over a 1.5 hour interval, the reaction was maintained at 90° C. for 1 hour with stirring; then the unreacted p-cresol was vacuum distilled from the reaction mixture. The para-cresol dicyclopentadiene (PCDP) resin was isolated by pouring into a stainless steel pan and allowing to cool to ambient temperature, yield 456.0 g; Mn=720, Mw=1900, dispersity of 2.64.

436.0 grams of the para-cresol dicyclopentadiene (PCDP) from above was dissolved in 1200 mL of N-methylpyrrolidinone (NMP) in a 2000 mL 3-neck round bottom flask equipped with mechanical stirrer, addition funnel, condenser, thermometer, nitrogen purge and Therm-O-Watch. To this reaction mixture was added 269.0 g (1.763 moles) of vinylbenzylchloride (60/40 para/meta isomer ratio) and 0.45 g of 2,6-di-tert-butyl-p-cresol (BHT). The reaction mixture was heated to 60° C. and 106.0 g (1.890 moles) of potassium hydroxide in 250 mL of methanol was added dropwise over a 2.5 hour interval. The reaction was maintained at 60° C. for 16 hrs with stirring under a nitrogen purge. To this reaction mixture was added 102.0 g (0.829 moles) of n-propylbromide was added to the reaction mixture and heated with stirring under purge to 60° C. To this reaction mixture was then added 35.4 g (0.631 moles) of potassium hydroxide in 120 mL of methanol over a 1.5 hour interval. The reaction was maintained at 60° C. for 3 hours and then allowed to cool to room temperature. The reaction mixture was then transferred to a separatory funnel, and 4 Liters of toluene added and then washed four times with 2.0 Liters of water and once with saturated sodium chloride solution, dried over sodium sulfate, filtered and concentrated under vacuum, yielding a red resinous product; Mn=780, Mw=1600, dispersity of 2.1.

EXAMPLE 6

Synthesis of Styrene Terminated Para-Cresol Dicyclopentadiene (STPCDP (70VBz/30Pr))

628.0 grams (5.807 moles) of para-cresol was charged into a 2000 mL 3-neck round bottom flask equipped with mechanical stirrer, addition funnel, condenser, thermometer, Therm-O-Watch, and Nitrogen purge. The reaction flask is heated to 90° C. under nitrogen with stirring. To the melted p-cresol is added 12.0 mL (0.082 moles) of boron trifluoride etherate. To this reaction mixture was added 524.0 g (3.963 moles) of dicyclopentadiene over a 3.0 hour interval, the reaction was maintained at 90° C. for 1 hour with stirring; then the unreacted p-cresol was vacuum distilled from the reaction mixture. The para-cresol dicyclopentadiene (PCDP) resin was isolated by pouring into a stainless steel pan and allowing to cool to ambient temperature, yielding 612.2 g of resin; Mn=990, Mw=2900, dispersity of 2.93.

591.2 grams of the para-cresol dicyclopentadiene (PCDP) from above was dissolved in 2100 mL of N-methylpyrrolidinone (NMP) in a 5000 mL 3-neck round bottom flask equipped with mechanical stirrer, addition funnel, condenser, thermometer, nitrogen purge and Therm-O-Watch To this reaction mixture was added 364.6 g (2.389 moles) of vinylbenzylchloride (60/40 para/meta isomer ratio) and 0.6 g of 2,6-di-tert-butyl-p-cresol (BHT). The reaction mixture was heated to 60° C. and 147.4 g (2.627 moles) of potassium hydroxide in 325 mL of methanol was added dropwise over a 2 hour interval. The reaction was maintained at 60° C. for 6 hrs with stirring under a nitrogen purge. To this reaction mixture was added 57.0 g (1.276 moles) of n-propylbromide, and then 71.82 g (1.280 moles) of potassium hydroxide in 165 mL of methanol was added over a 2 hour interval. The reaction was maintained at 60° C. for 4 hours and then allowed to cool to room temperature. The reaction mixture was then transferred to a separatory funnel, and 4.0 Liters of toluene added and then washed thrice with 2.0 Liters of water, dried over sodium sulfate, filtered and concentrated under vacuum, yielding a red resinous product; Mn=740, Mw=1500, dispersity of 2.03.

EXAMPLE 7

Synthesis of Styrene Terminated Para-Cresol Dicyclopentadiene (STPCDP (70VBz/30Pr))

500.0 grams of para-cresol dicyclopentadiene (PCDP) from Borden Chemical (Mn=520, Mw=1100, dispersity of 2.12) and 500 mL of ortho-dichlorobenzene was charged into a 2000 mL 3-neck round bottom flask equipped with mechanical stirrer, addition funnel, condenser, thermometer, Therm-O-Watch, and Nitrogen purge. The reaction mixture was heated to 60° C. under nitrogen with stirring; after complete dissolution of PCDP then 1.0 mL ($6.83 \times 10^{-3}$ moles) of boron trifluoride etherate was added. To this reaction mixture was added 71.12 g (0.538 moles) of dicyclopentadiene over a 45 minute interval, the reaction was maintained at 60° C. with stirring during the addition; then the reaction was heated to 150° C. for 4 hours, and then cooled to ambient temperature. The reaction mixture was coagulated by addition to methanol, filtered, and then dried in a vacuum oven at 80° C. overnight; Mn=700, Mw=1500, dispersity of 2.14.

308.0 grams of the para-cresol dicyclopentadiene (PCDP) from above was dissolved in 1050 mL of N-methylpyrrolidinone (NMP) in a 2000 mL 3-neck round bottom flask equipped with mechanical stirrer, addition funnel, condenser, thermometer, nitrogen purge and Therm-O-Watch. To this reaction mixture was added 189.0 g (1.238 moles) of vinylbenzylchloride (60/40 para/meta isomer ratio) and 0.20 g of 2,6-di-tert-butyl-p-cresol (BHT). The reaction mixture was heated to 60° C. and 76.82 g (1.370 moles) of potassium hydroxide in 225 mL of methanol was added dropwise over a 1.75 hour interval. The reaction was maintained at 60° C. for 4.2 hrs with stirring under a nitrogen purge. To this reaction mixture was added 78.83 g (0.640 moles) of n-propylbromide, and then 35.91 g (0.640 moles) of potassium hydroxide in 125 mL of methanol added over a 2.0 hour interval. The reaction was maintained at 60° C. for 16 hours and then allowed to cool to room temperature. The reaction mixture was then transferred to a separatory funnel, and 3 Liters of toluene added and then washed thrice with 2.0 Liters of water, dried over magnesium sulfate, filtered and concentrated under vacuum, yielding 332.0 g of red resinous product; Mn=670, Mw=1300, dispersity of 1.9.

EXAMPLE 8

Synthesis of Styrene Terminated Para-Cresol Dicyclopentadiene (STPCDP (65VBz/35Pr))

500.0 grams of para-cresol dicyclopentadiene (PCDP) from Borden Chemical (Mn=520, Mw=1100, dispersity of 2.12) and 500 mL of ortho-dichlorobenzene was charged into a 2000 mL 3-neck round bottom flask equipped with mechanical stirrer, addition funnel, condenser, thermometer, Therm-O-Watch, and Nitrogen purge. The reaction mixture was heated to 60° C. under nitrogen with stirring; after complete dissolution of PCDP then 1.0 mL ($6.83 \times 10^{-3}$ moles) of boron trifluoride etherate was added. To this reaction mixture was added 59.26 g (0.448 moles) of dicyclopentadiene over a 2 hour interval, the reaction was maintained at 60° C. with stirring during the addition; then the reaction was heated to 150° C. for 4 hours, and then cooled to ambient temperature. The reaction mixture was coagulated by addition to methanol, filtered, and then dried in a vacuum oven at 80° C. overnight; Mn=630, Mw=1400, dispersity of 2.22.

146.22 grams of the para-cresol dicyclopentadiene (PCDP) from above was dissolved in 600 mL of N-methylpyrrolidinone (NMP) in a 2000 mL 3-neck round bottom flask equipped with mechanical stirrer, addition funnel, condenser, thermometer, nitrogen purge and Therm-O-Watch. To this reaction mixture was added 4.76 g (0.424 moles) of vinylbenzylchloride (60/40 para/meta isomer ratio) and 0.15 g of 2,6-di-tert-butyl-p-cresol (BHT). The reaction mixture was heated to 60° C. and 23.81 g (0.424 moles) of potassium hydroxide in 60 mL of methanol was added dropwise over an 1.2 hour interval. The reaction was maintained at 60° C. for 4.0 hrs with stirring under a nitrogen purge. To this reaction mixture was added 40.14 g (0.326 moles) of n-propylbromide, and then added 18.32 g (0.327 moles) of potassium hydroxide in 40 mL of methanol added over an hour interval. The reaction was maintained at 60° C. for 4 hours and then allowed to cool to room temperature. The reaction mixture was then transferred to a separatory funnel, and 1 Liter of toluene added and then washed thrice with 1 Liter of water, dried over sodium sulfate, filtered and concentrated under vacuum, yielding a red resinous product; Mn=710, Mw=1400, dispersity of 1.97.

EXAMPLE 9

Synthesis of Styrene-Terminated Tetraphenol Ethane (70% Vinylbenzyl/30% Propyl)(STTPE(70 VBz/30 Pr))

To a 250 mL round bottom, 3-neck flask equipped with a stirring shaft, an addition funnel and a condenser was added 25.0 g tetraphenol ethane (TPE) (Mn=274, Mw=711) (0.0354 mol), 0.23 g BHT (0.00106 mol) and 120 mL N-methyl pyrollidinone (NMP). Upon dissolution of the TPE, 26.48 g vinylbenzyl chloride (VBC)(0.174 mol) were added and the vessel flushed and placed under positive nitrogen pressure by means of a mineral oil bubbler. The solution was heated to 60° C. by means of a water bath and 11.34 g KOH (0.177 mol) dissolved in 25 mL of methanol were added dropwise over 30 minutes. The mixture was kept at 60° C. for an additional 3.5 hours, 9.0 mL 1-bromopropane (0.099 mol) were then added. 4.86 g KOH (0.0758 mol) dissolved in 11 mL methanol were then added dropwise over 30 minutes and the temperature maintained at 50° C. an additional 1.5 hours.

The mixture was cooled and slowly added to 600 mL of methanol leaving a solid yellow mass. The methanol was decanted and the solids along with fresh methanol were placed in a blender to produce an oily solid which was collected on a Buchner funnel. This material was dissolved in dichloromethane and washed with $4 \times 500$ mL water. The organic phase was dried over sodium sulfate and filtered through Celite. Solvent was removed by rotary evaporation leaving an orange semisolid, 49% yield. GPC examination of resin indicates Mn=1040, Mw=1290, dispersity 1.24. Infrared examination of resin indicates some residual OH (<5%), ion chromatography indicates: 17 ppm Cl-, <1 ppm Br-, 1 ppm $SO_4^{-2}$.

EXAMPLE 10

Synthesis of Styrene Terminated Tetraphenol Ethane (100% Vinylbenzyl)(STTPE (100 VBz))

To a 2-L, 3-neck round bottom flask equipped with a stirring shaft, an additional funnel and a condenser was added 200.0 g tetraphenol ethane (TPE) (Mn=274, Mw=711)(0.284 mol), 1.88 g BHT (0.00852 mol) and 950 mL N-methyl pyrollidinone (NMP). Upon dissolution of the TPE 242.65 g vinylbenzyl chloride (VBC) (1.59 mol) were added and the vessel flushed and placed under positive nitrogen pressure by means of a mineral oil bubbler. The solution was heated to 60° C. by a water bath and 101.95 g KOH (1.59 mol) dissolved in 230 mL of methanol were added dropwise over 30 minutes. The mixture was kept at 60° C., for an additional 4.7 hours, 15.17 g VBC (0.0994 mol) were then added. 6.37 g KOH (0.0994 mol) dissolved in 15 mL methanol were then added dropwise. A final identical addition of VBC and KOH/methanol was made 1.7 hours later and the reaction maintained at 60° C. for 1 hour longer.

The mixture was cooled and 1.2 L toluene were added. The mixture was washed with $1 \times 3$ L water and $2 \times 3$ L 1 M NaCl (aq). The organic phase was dried over sodium sulfate, slurried with Celite and filtered. Solvent was removed by rotary evaporation up to 40° C. at 3 torr leaving a viscous brown resin, 95% yield. GPC analysis found Mn=778, Mw=1079, dispersity 1.39; Infrared analysis indicates no residual hydroxyl (<0.5%); Ion Chromatography found: 45 ppm Cl-.

EXAMPLE 11

Preparation of crosslinked polymer; thermal curing

The styrene terminated para-cresol dicyclopentadiene (STPCDP) and styrene terminated tetraphenol ethane (STTPE) prepared as described in Examples 4 and 9, respectively, were thermally cured using the following cure cycle: 2 hours at 80° C., 100° C. for 16 hours, 120° C. for 4 hours, 160° C. for 16 hours, 200° C. for 2 hours, and 225° C. for 1 hour. Some properties of the resulting cured mixed resins are summarized in the following table.

TABLE A

| SAMPLE NO. | 1 | 2 | 3 |
|---|---|---|---|
| STPCDP/STTPE | (90/10) | (75/25) | (50/50) |
| Tg (°C)[a] | >300 | >300 | >300 |
| Tsp (°C)[b] | 147 ± 3 | 160 ± 4 | 161 ± 2 |
| $\alpha_{sp}$ (ppm/°C)[c] | 75 ± 3 | 70 ± 9 | 74 ± 2 |
| $\alpha_{260}$ (ppm/°C)[d] | 167 ± 1 | 110 ± 14 | 93 ± 2 |
| $\epsilon'$[e] | 2.75 | 2.79 | 2.77 |
| tan δ[f] | 0.0003 | 0.0005 | 0.003 |
| $\epsilon'$[g] | 2.76 | 2.85 | 2.77 |
| tan δ[h] | 0.002 | 0.001 | 0.0008 |
| % Water Absorption[i] | 0.102 | 0.110 | 0.136 |
| Modulus (GPa)[j] | 9.1 | 9.2 | 8.9 |
| Tg (°C)[k] | >200 | >200 | >200 |

[a] glass transition temperature by differential scanning calorimeter
[b] softening point by Thermo Mechanical Analysis - minor thermal transition
[c] coefficient of thermal expansion between 25° C. and softening point
[d] coefficient of thermal expansion between 25° C. and 260° C.
[e] dielectric constant at 1 MHz and 0% Relative Humidity at 25° C.
[f] loss tangent at 1 MHz and 0% Relative Humidity at 25° C.
[g] dielectric constant at 1 MHz and 50% Relative Humidity at 25° C.
[h] loss tangent at 1 MHz and 50% Relative Humidity at 25° C.
[i] at 50% Relative Humidity, 25° C. for 168 hours
[j] modulus measured from -125° C. to 200° C. at 4 Hz
[k] glass transition temperature by DMA at 4 Hz range scanned -125° C. to 200° C.

EXAMPLE 12

A series of coating solutions were prepared and used to coat silicon surfaces. The solution concentrations were between 50.8 and 53.1 wt. % STPCDP (Example 5) and STTPE (in Example 9) in toluene. The solutions were applied by spin coating at 900-950 rpm for 60 seconds. The coated discs were soft baked at 25° C. for 18 hours under vacuum. Then, they were exposed for 3 minutes to UV irradiation with a 300 watt mercury vapor lamp with a quartz/water filter. The irradiated coatings were then exposed to various solvents and the amount of cured resin dissolved was measured. The results are shown in the following tables.

TABLE B

| | % STPCDP/STTPE[a] Removed Solvent (Toluene:Ethanol)[b] | | | | | |
|---|---|---|---|---|---|---|
| Time (sec) | 100:0 | 80:20 | 60:40 | 40:60 | 20:80 | 0:100 |
| 0 | 0 | 0 | 0 | 0 | 0 | 0 |
| 30 | 3.59 | 6.29 | 11.30 | 9.42 | 26.98 | 0.34 |
| 60 | 2.99 | 7.86 | 12.62 | 11.69 | 30.16 | 0.00 |
| 90 | 6.29 | 10.38 | 13.95 | 14.94 | 34.60 | 2.03 |
| 120 | 6.59 | 10.69 | 15.28 | 16.56 | 35.24 | 2.03 |
| 180 | 8.08 | 11.32 | 16.28 | 16.56 | 35.24 | 1.69 |
| 300 | 5.39 | 9.12 | 15.61 | 17.86 | 34.92 | 0.68 |

[a] 90 STPCDP/10 STTPE by weight coated on silicon wafer and soft baked at 25° C. for 18 hrs., 3 minute cure 300 Watt Mercury Vapor Lamp with quartz/water filter.
[b] Weight % solutions.

TABLE C

| | % STPCDP/STTPE[a] Removed Solvent (Toluene:n-Hexane)[b] | | | | | |
|---|---|---|---|---|---|---|
| Time (sec) | 100:0 | 80:20 | 60:40 | 40:60 | 20:80 | 0:100 |
| 0 | 0 | 0 | 0 | 0 | 0 | 0 |
| 30 | 3.59 | -1.71 | -2.76 | 0.36 | 0.34 | -0.66 |
| 60 | 2.99 | -1.71 | 5.17 | 2.87 | -0.67 | -2.32 |
| 90 | 6.29 | -2.05 | 15.17 | 8.24 | 2.69 | -0.33 |
| 120 | 6.59 | -1.71 | 18.62 | 15.41 | 6.73 | -0.66 |
| 180 | 8.08 | -2.05 | 21.38 | 23.66 | 14.81 | 0.00 |
| 300 | 5.39 | -3.07 | 24.83 | 28.32 | 25.25 | 1.99 |

[a] 90 STPCDP/10 STTPE by weight coated on silicon wafer and soft baked at 25° C. for 18 hrs., 3 minute cure 300 Watt Mercury Vapor Lamp with quartz/water filter.
[b] Weight % solutions.

Tables B and C may be compared with the results of Tables D and E below in which the soft bake was carried out and no curing by UV radiation was done.

TABLE D

| | % STPCDP/STTPE[a] Removed Solvent (Toluene:Ethanol)[b] | | | | | |
|---|---|---|---|---|---|---|
| Time (sec) | 100:0 | 80:20 | 60:40 | 40:60 | 20:80 | 0:100 |
| 0 | 0 | 0 | 0 | 0 | 0 | 0 |
| 30 | 99.08 | 99.32 | 100.00 | 41.55 | 96.92 | 1.72 |
| 60 | 98.16 | 98.98 | 99.34 | 53.72 | 99.32 | 1.03 |
| 90 | 100.61 | 100.68 | 101.97 | 71.28 | 100.34 | 1.37 |
| 120 | 99.69 | 101.36 | 100.99 | 73.31 | 100.00 | 2.06 |
| 180 | 100.92 | 100.68 | 100.00 | 77.70 | 100.68 | 2.41 |
| 300 | 99.69 | 100.34 | 100.33 | 79.05 | 99.32 | 2.41 |

[a] 90 STPCDP/10 STTPE by weight coated on silicon wafer and soft baked at 25° C. for 18 hrs.
[b] Weight % solutions.

TABLE E

| | % STPCDP/STTPE[a] Removed Solvent (Toluene:n-Hexane)[b] | | | | | |
|---|---|---|---|---|---|---|
| Time (sec) | 100:0 | 80:20 | 60:40 | 40:60 | 20:80 | 0:100 |
| 0 | 0 | 0 | 0 | 0 | 0 | 0 |
| 30 | 99.08 | 102.14 | 13.57 | -3.03 | 1.69 | -0.70 |
| 60 | 98.16 | 101.42 | 91.79 | 30.64 | -1.36 | -1.75 |
| 90 | 100.61 | 101.07 | 98.57 | 78.11 | 8.81 | -1.05 |
| 120 | 99.69 | 102.49 | 98.57 | 95.62 | 29.83 | 0.35 |
| 180 | 100.92 | 101.42 | 99.64 | 97.31 | 62.03 | 0.70 |
| 300 | 99.69 | 101.78 | 100.00 | 99.66 | 76.95 | 3.15 |

[a] 90 STPCDP/10 STTPE by weight coated on silicon wafer and soft baked at 25° C. for 18 hrs.
[b] Weight % solutions.

TABLE F

| | % STPCDP/STTPE[a] Removed Solvent (Toluene:Ethanol)[b] | | | | | |
|---|---|---|---|---|---|---|
| Time (sec) | 100:0 | 80:20 | 60:40 | 40:60 | 20:80 | 0:100 |
| 0 | 0 | 0 | 0 | 0 | 0 | 0 |
| 30 | 53.97 | 64.84 | 64.38 | 20.00 | -2.05 | 0.00 |
| 60 | 69.21 | 70.33 | 70.21 | 30.36 | -2.05 | -1.39 |
| 90 | 70.86 | 73.63 | 70.89 | 37.50 | -0.68 | -1.39 |
| 120 | 71.85 | 71.79 | 71.58 | 42.50 | -1.02 | 0.69 |
| 180 | 71.85 | 74.36 | 72.95 | 45.36 | -1.37 | 0.35 |
| 300 | 74.83 | 74.73 | 73.29 | 50.71 | 0.34 | 0.35 |

[a] 75 STPCDP/25 STTPE by weight coated on silicon wafer and soft baked at 25° C. for 18 hrs., 3 minute cure 300 Watt Mercury Vapor Lamp with quartz/water filter.
[b] Weight % solutions.

TABLE G

| | % STPCDP/STTPE[a] Removed Solvent (Toluene:n-Hexane)[b] | | | | | |
|---|---|---|---|---|---|---|
| Time (sec) | 100:0 | 80:20 | 60:40 | 40:60 | 20:80 | 0:100 |
| 0 | 0 | 0 | 0 | 0 | 0 | 0 |
| 30 | 53.97 | 69.47 | 0.73 | -1.10 | 1.01 | -0.70 |
| 60 | 69.21 | 73.33 | 18.18 | 8.46 | -0.34 | -1.76 |
| 90 | 70.86 | 77.89 | 42.55 | 30.15 | 0.34 | -2.82 |
| 120 | 71.85 | 78.25 | 48.73 | 41.54 | 1.35 | -1.41 |
| 180 | 71.85 | 78.25 | 52.36 | 51.84 | 3.03 | -1.06 |
| 300 | 74.83 | 81.40 | 54.55 | 60.29 | 6.40 | -1.76 |

[a] 75 STPCDP/25 STTPE by weight coated on silicon wafer and soft baked at 25° C. for 18 hrs., 3 minute cure 300 Watt Mercury Vapor Lamp with quartz/water filter.
[b] Weight % solutions.

Tables F and G may be compared with the results of Tables H and I below in which only a soft bake was carried out and no curing by UV radiation was done.

TABLE H

| | % STPCDP/STTPE[a] Removed Solvent (Toluene:Ethanol)[b] | | | | | |
|---|---|---|---|---|---|---|
| Time (sec) | 100:0 | 80:20 | 60:40 | 40:60 | 20:80 | 0:100 |
| 0 | 0 | 0 | 0 | 0 | 0 | 0 |
| 30 | 96.10 | 98.98 | 89.66 | 28.09 | 0.68 | 2.42 |
| 60 | 99.29 | 101.36 | 98.62 | 47.16 | 3.74 | 2.42 |
| 90 | 99.65 | 99.66 | 99.66 | 57.53 | 5.78 | 1.04 |
| 120 | 99.65 | 100.34 | 100.00 | 64.55 | 6.12 | 2.08 |
| 180 | 99.29 | 99.32 | 99.31 | 69.90 | 9.18 | 2.08 |
| 300 | 100.35 | 100.34 | 99.31 | 75.25 | 10.88 | 1.38 |

[a] 75 STPCDP/25 STTPE coated on silicon wafer and soft baked at 25° C. for 18 hrs.
[b] Weight % solutions.

TABLE I

| | % STPCDP/STTPE[a] Removed Solvent (Toluene:n-Hexane)[b] | | | | | |
|---|---|---|---|---|---|---|
| Time(sec) | 100:0 | 80:20 | 60:40 | 40:60 | 20:80 | 0:100 |
| 0 | 0 | 0 | 0 | 0 | 0 | 0 |
| 30 | 96.10 | 59.52 | −2.00 | −5.35 | −0.33 | 1.00 |
| 60 | 99.29 | 98.96 | 54.00 | 10.37 | −3.92 | 1.00 |
| 90 | 99.65 | 99.65 | 85.00 | 46.82 | 3.92 | 0.33 |
| 120 | 99.65 | 100.35 | 95.00 | 74.25 | 7.52 | 0.33 |
| 180 | 99.29 | 99.65 | 98.67 | 87.96 | 16.99 | 0.33 |
| 300 | 100.35 | 100.35 | 99.00 | 95.99 | 35.62 | 0.33 |

[a] 75 STPCDP/25 STTPE by weight coated on silicon wafer and soft baked at 25° C. for 18 hrs.
[b] Weight % solutions.

TABLE J

| | % STPCDP/STTPE[a] Removed Solvent (Toluene:Ethanol)[b] | | | | | |
|---|---|---|---|---|---|---|
| Time (sec) | 100:0 | 80:20 | 60:40 | 40:60 | 20:80 | 0:100 |
| 0 | 0 | 0 | 0 | 0 | 0 | 0 |
| 30 | 2.56 | 10.84 | 3.73 | −2.69 | −2.60 | −1.86 |
| 60 | 3.66 | 15.38 | 10.45 | −0.38 | −1.49 | −1.12 |
| 90 | 7.69 | 17.83 | 14.18 | 3.85 | −2.97 | 0.00 |
| 120 | 12.09 | 18.53 | 18.66 | 3.85 | −0.74 | −1.12 |
| 180 | 13.19 | 20.98 | 18.66 | 6.54 | −0.37 | 1.86 |
| 300 | 14.65 | 23.08 | 27.99 | 11.54 | 10.04 | 0.00 |

[a] 50 STPCDP/50 STTPE by weight coated on silicon wafer and soft baked at 25° C. for 18 hrs., 3 minute cure 300 Watt Mercury Vapor Lamp with quartz/water filter.
[b] Weight % solutions.

TABLE K

| | % STPCDP/STTPE[a] Removed Solvent (Toluene:n-Hexane)[b] | | | | | |
|---|---|---|---|---|---|---|
| Time (sec) | 100:0 | 80:20 | 60:40 | 40:60 | 20:80 | 0:100 |
| 0 | 0 | 0 | 0 | 0 | 0 | 0 |
| 30 | 2.56 | 1.13 | 0.00 | −0.39 | 0.00 | −0.37 |
| 60 | 3.66 | 2.26 | 1.84 | 2.33 | 1.57 | 0.00 |
| 90 | 7.69 | 3.02 | 1.84 | −0.39 | 0.39 | 0.00 |
| 120 | 12.09 | 3.40 | 2.94 | 1.95 | 1.18 | 0.00 |
| 180 | 13.19 | 7.55 | 2.94 | 1.95 | 0.78 | 0.00 |
| 300 | 14.65 | 10.94 | 2.94 | 3.11 | 3.14 | 0.00 |

[a] 50 STPCDP/50 STTPE by weight coated on silicon wafer and soft baked at 25° C. for 18 hrs., 3 minute cure 300 Watt Mercury Vapor Lamp with quartz/water filter.
[b] Weight % solutions.

Table J and K may be compared with the results of Tables L and M below in which only the soft bake was carried out and no curing by UV radiation was done.

TABLE L

| | % STPCDP/STTPE[a] Removed Solvent (Toluene:Ethanol)[b] | | | | | |
|---|---|---|---|---|---|---|
| Time (sec) | 100:0 | 80:20 | 60:40 | 40:60 | 20:80 | 0:100 |
| 0 | 0 | 0 | 0 | 0 | 0 | 0 |
| 30 | 97.03 | 102.24 | 95.47 | 37.36 | −1.57 | −2.14 |
| 60 | 100.74 | 99.63 | 98.87 | 65.66 | 3.54 | 0.00 |
| 90 | 101.12 | 99.63 | 99.62 | 73.58 | 5.12 | −0.71 |
| 120 | 100.37 | 99.25 | 99.25 | 80.75 | 7.48 | −1.42 |
| 180 | 101.12 | 98.88 | 98.11 | 83.40 | 10.24 | −3.20 |
| 300 | 101.12 | 98.88 | 101.13 | 87.55 | 15.75 | −0.71 |

[a] 50 STPCDP/50 STTPE coated on silicon wafer and soft baked at 25° C. for 18 hrs.
[b] Weight % solutions.

TABLE M

| | % STPCDP/STTPE[a] Removed Solvent (Toluene:n-Hexane)[b] | | | | | |
|---|---|---|---|---|---|---|
| Time (sec) | 100:0 | 80:20 | 60:40 | 40:60 | 20:80 | 0:100 |
| 0 | 0 | 0 | 0 | 0 | 0 | 0 |
| 30 | 97.03 | 99.25 | −3.18 | −3.04 | 0.35 | −0.71 |
| 60 | 100.74 | 103.02 | 39.93 | −0.38 | 0.70 | −1.79 |
| 90 | 101.12 | 101.51 | 91.87 | 14.45 | 5.61 | −0.71 |
| 120 | 100.37 | 102.64 | 98.94 | 56.27 | 12.98 | 0.00 |
| 180 | 101.12 | 104.15 | 98.23 | 80.23 | 20.70 | 0.00 |
| 300 | 101.12 | 103.77 | 99.29 | 92.02 | 35.09 | −0.36 |

[a] 50 STPCDP/50 STTPE by weight coated on silicon wafer and soft baked at 25° C. for 18 hrs.
[b] Weight % solutions.

EXAMPLE 13

A series of 50% STPCDP (Example 6) and 50% STTPE (Example 9) solutions were prepared in toluene were prepared at different concentrations ranging from 46.0 Wt. % solids to 58.4 Wt. % solids. These solutions were spin coated onto a silicon substrate (surface) utilizing spin coating rates from 700 rpm to 1500 rpm for 60 seconds; soft baked for 24 hours at 25° C. under vacuum. The samples were then exposed for 3 minutes to UV irradiation with a 300 watt mercury lamp employing an USAF Test Pattern and a quartz/water filter. The photocured polymer was then developed with toluene for 1 minute at 25° C. The air dried substrate was hard baked employing a cure cycle under vacuum of 25° C. to 220° C. ramp in 1 hour, held at 220° C. for 2.5 hours and then cooled to room temperature.

The film thickness of the photocured polymer was analyzed employing a Taylor-Hobson Talysurf 10 profilometer. The following table illustrates the film thicknesses obtained.

TABLE N

| 50 STPCDP/50 STTPE Solids Content[a] | Viscosity (mPa s) | Film Thickness (μm) Spin Coating Speed (rpm) | | |
|---|---|---|---|---|
| | | 700 | 1000 | 1500 |
| 46.0 | 6.0 | 5.3 | 4.4 | 4.2 |
| 48.9 | 10.0 | 7.5 | 6.3 | 4.7 |
| 53.5 | 16.0 | 10.5 | 8.2 | 6.8 |
| 58.4 | 32.0 | — | 12.9 | 10.9 |

[a] Dissolved solids content in Toluene

EXAMPLE 14

A 56 Wt. % solids solution of 50% STPCDP, 50% STTPE solution was prepared in toluene using of STPCDP of Example 6 and STTPE of Example 9. This solution was spin coated onto a silicon substrate (surface) utilizing spin coating rates from 600 rpm to 2000 rpm for 60 seconds; soft baked for 24 hours at 25° C. under vacuum. The samples were then exposed for 3 minutes to UV irradiation with a 300 watt mercury lamp employing an USAF Test Pattern and a quartz- /water filter. The photocured polymer was then developed with toluene for minute at 25° C. The air dried substrate was hard baked employing a cure cycle under vacuum of 25° C. to 219° C. ramp in 1 hour, held at 219° C. for 2.5 hours and then cooled to room temperature.

The film thickness and sidewall angle of the photocured polymer was analyzed utilizing a Sloan Technology Corporation Dektak 3030 profilometer. This data is summarized in the following table.

TABLE G

| Spin Speed (rpm) | Film thickness (μm) | Sidewall Angle |
|---|---|---|
| 600 | 13.5 | 19 |
| 600 | 13.5 | 20 |
| 700 | 12.0 | 35 |
| 700 | 12.0 | 30 |
| 800 | 12.3 | 33 |
| 800 | 11.2 | 21 |
| 800 | 11.3 | 35 |
| 800 | 12.0 | 18 |
| 1000 | 10.3 | 24 |
| 1000 | 10.5 | 28 |
| 1000 | 10.0 | 33 |
| 1000 | 11.2 | 26 |
| 1500 | 8.5 | 22 |
| 1500 | 8.8 | 30 |
| 1500 | 9.2 | 26 |
| 1500 | 12.4 | 18 |
| 2000 | 7.5 | 25 |
| 2000 | 7.7 | 9 |
| 2000 | 7.9 | 37 |
| 2000 | 8.0 | 20 |

EXAMPLE 15

A series of 50% STPCDP (Example 6) and 50% STTPE (Example 9) solutions were prepared in toluene were prepared at different concentrations ranging from 46.0 Wt. % solids to 58.4 Wt. % solids. These solutions were spin coated onto a silicon substrate (surface) utilizing spin coating rates from 700 rpm to 1500 rpm for 60 seconds; soft baked for 24 hours at 25° C. under vacuum. The samples were then exposed for 3 minutes to UV irradiation with a 300 watt mercury lamp employing an USAF Test Pattern and a quartz/water filter. The photocured polymer was then developed with toluene for minute at 25° C. The air dried substrate was hard baked employing a cure cycle under vacuum of 25° C. to 220° C. ramp in 1 hour, held at 220° C. for 2.5 hours and then cooled to room temperature. The samples were then metallized via ion-beam sputtering to yield a metal film of thickness 5000 to 10000Å.

The adhesion was evaluated via a calibrated "Scotch-Tape" adhesion test before and after thermal shock cycling. A thermal shock cycle encompasses the following thermal cycling of the sample: hold at −55° C. for 10 minutes, −55° C. to 125° C. over a rapid ramp, hold at 125° C. for 10 minutes. In the following tables the ratio given means that of 25 squares of the metal, some to all of them were not removed by the tape. That is, 5/25 means that 20 squares of metal were removed.

| | Adhesion Measurements Results | | | | | |
|---|---|---|---|---|---|---|
| | Before Thermal Shock Cycling | | After 92 Cycles | | After 184 Cycles | |
| Metal Layer | 2.5 lb.[b] | 10.0 lb. | 2.5 lb. | 10.0 lb. | 2.5 lb. | 10.0 lb. |
| Chromium | 0/25 Passed | — | — | — | — | — |
| Chromium | 0/25 | — | — | — | — | — |
| Copper | Passed 0/25 | — | — | — | — | — |
| Copper | Passed 0/25 | — | — | — | — | — |
| Copper | Passed 0/25 | — | — | — | — | — |
| Aluminum | Passed 1/25 Passed | 0/1 Passed | — | — | — | — |
| Aluminum | 0/25 Passed | — | — | — | — | — |
| Gold | 6/25 Passed | 6/6 Passed | a | a | a | a |
| Gold | 0/25 Passed | — | — | — | — | — |
| Nickel | 0/25 Passed | — | — | — | — | — |
| Nickel | 0/25 Passed | — | — | — | — | — |

[a]Sample not evaluated.
[b]Tape rating in lb for ¼ inch wide tape

EXAMPLE 16

STPCDP resin of Example 5 and STTPE of Example 9 was dissolved in toluene to yield a solution of (50:50 STPCDP:STTPE) composition 28.0 Wt. % STPCDP, 28.0 Wt. % STTPE and 44 Wt. % toluene. This solution was spin coated onto an alumina or silicon substrate (surface) utilizing spin coating rate of 1000 rpm for 60 seconds; soft baked for 1 hour at 60° C. under nitrogen. The polymer was hard baked employing a cure cycle under nitrogen of 25° C. to 220° C. ramp in 3 hour, held at 220° C. for 2.0 hours and then ramped from 220° C. to 25° C. in 4 hours.

The adhesion was evaluated via a calibrated "Scotch-Tape" adhesion test before and after thermal shock cycling. A thermal shock cycle encompasses the following thermal cycling of the sample: hold at −55° C. for 10 minutes, −55° C. to 125° C. over a rapid ramp, hold at 125° C. for 10 minutes.

| | Adhesion Measurements Results | | | |
|---|---|---|---|---|
| | Before Thermal Shock Cycling | | After 92 Cycles | |
| Substrate | 2.5 lb. | 10.0 lb. | 2.5 lb. | 10.0 lb. |
| Alumina | 0/25 Passed | — | — | — |
| Silicon | 0/25 Passed | — | — | — |

EXAMPLE 17

STPCDP resin of Example 5 and STTPE of Example 9 was dissolved in toluene to yield a solution of (50:50 STPCDP:STTPE) composition 28.0 Wt. % STPCDP, 28 Wt. % STTPE and 44 Wt. % toluene. This solution was spin coated onto an alumina substrate (surface) onto which had been ion-sputtered with a metal film of thickness 5000Å, utilizing spin coating rate of 1000 rpm for 60 seconds; soft baked for 1 hour at 60° C. under nitrogen. The polymer was hard baked employing a cure cycle under nitrogen of 25° C. to 220° C. ramp in 3 hours, held at 220° C. for 2.0 hours and then ramped from 220° C. to 25° C. in 4 hours.

The adhesion was evaluated via a calibrated "Scotch-Tape" adhesion test before and after thermal shock cycling. A thermal shock cycle encompasses the following thermal cycling of the sample: hold at $-55°$ C. for 10 minutes, $-55°$ C. to $125°$ C. over a rapid ramp, hold at $125°$ C. for 10 minutes.

| Metal Layer | Adhesion Measurements Results | | | |
|---|---|---|---|---|
| | Before Thermal Shock Cycling | | After 92 Cycles | |
| | 2.5 lb | 10.0 lb | 2.5 lb. | 10.0 lb |
| Chromium | 25/25 Passed | 25/25 Passed | (a) | (a) |
| Nickel | 0/25 Passed(b) | — | — | — |
| Copper | 0/25 Passed(b) | — | — | — |
| Aluminum | 0/25 Passed(b) | — | — | — |
| Gold | 0/25 Passed(b) | — | — | — |

(a)Sample not evaluated.
(b)Failed at polymer to metal interface.

It can be seen in the above Examples 15-17 that chromium adhered particularly well to the dielectric polymers and thus can serve as a suitable base for copper layers which provide conductive patterns in the multilevel structures:

We claim:

1. A method of forming a polymer on a substrate in a predetermined pattern comprising:
    (a) coating a substrate with a mixture of prepolymers which comprises
        (1) an ether of the reaction product of dicyclopentadiene with phenol having the formula

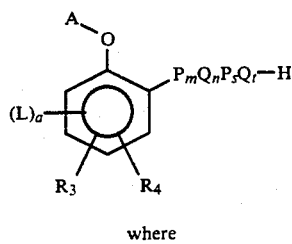

where

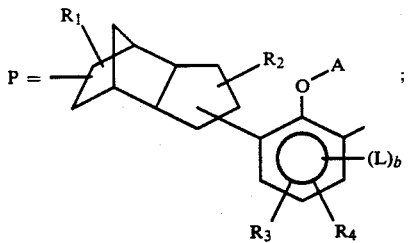

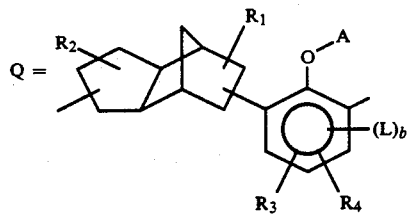

with
$R_1$, $R_2$ = H or alkyl of 1-10 carbon atoms;
$R_3$ = methyl;
$R_4$ = H;
A = H,

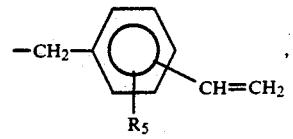

an alkyl moiety containing 1 to 10 carbon atoms, a cycloalkyl moiety having 5 to 10 carbon atoms, or benzyl;
L = Br or Cl;
a = 0, 1, or 2;
b = 0 or 1;
m, n, s, and t are 0 or an integer, and $m+n+s+t=z$ is an integer from 1-10; and
$R_3$ = H, an alkyl moiety of 1-10 carbon atoms, a halogen or alkoxy moiety, or a monovalent aromatic radical;
    (2) an ether of the oligomeric condensation product of
        a) molar proportion of a dialdehyde and
        b) from about 3 to about 4 molar proportions of a phenol; when the dialdehyde is selected from the group consisting of $OHC(CH_2)_rCHO$, where $r=0$ or an integer from 1 to 6, cyclopentanedialdehyde, phthalaldehyde, isophthalaldehyde, terephthalaldehyde, hexahydrophthalaldehyde, cycloheptanedialdehyde, hexahydroisophthalaldehyde, hexahydroterephthalaldehyde, and cyclooctanedialdehyde; where the phenol has the structure $R_6C_6H_4$ and
    $R_6$ is hydrogen or an alkyl group containing from 1 to about 10 carbon atoms; and where the phenol residue of said oligomeric condensation product is etherified with one or more substituents to afford ether moieties randomly selected from the group consisting of vinylbenzyl, alkyl moieties containing from 1 to 10 carbon atoms, cycloalkyl moieties from 5 to 10 carbon atoms, and benzyl, with the ratio of vinylbenzyl to other moieties being from 1:1 to about 6:1;
    (b) irradiating the coated prepolymer of (a) through a masking pattern to selectively crosslink the portion of said coating being irradiated;
    (c) selectively dissolving the non-irradiated part of the prepolymer coating of (a); and
    (d) curing the crosslinked portion of the prepolymer coating by heating at a temperature in the range of $100°$ to $300°$ C. for a time sufficient to further crosslink said crosslinked coating and to transform the prepolymer to an infusible glassy solid.

2. The method of claim 1 wherein R and $R_6$ are hydrogen.
3. The method of claim 1 wherein Z is 3 or 4.
4. The method of claim 1 wherein A is para vinyl benzyl.
5. The method of claim 1 wherein L is Br.
6. The method of claim 1 wherein 70% of A is vinyl benzyl and the remainder is propyl.
7. The method of claim 1 wherein the dialdehyde is $OHC(CH_2)_rCHO$ and r is 0 or an integer from 1 to 6.
8. The method of claim 7 where r is 0.
9. The method of claim 1 wherein $R_6$ is hydrogen.
10. The method of claim 1 wherein $R_6$ is methyl.
11. The method of claim 1 wherein the ether moieties of the condensation product (2) are about 70% vinyl benzyl and 30% propyl.

12. The method of claim 1 wherein the molecular weight of condensation product (2) is 400 to 6000.

13. The method of claim 1 wherein the coating of (a) is softbaked before the irradiation of (b).

14. The method of claim 1 wherein the coating of (a) includes a photosensitizer or photoinitiator.

15. The method of claim 1 wherein the irradiation of (b) has a wavelength of 200 to 500 nm.

16. An electronic interconnect structure comprising the cured polymer prepared by the method of claim 1.

17. An electronic interconnect structure of claim 16 wherein said cured polymer is adhered to a layer of chromium metal.

* * * * *

UNITED STATES PATENT AND TRADEMARK OFFICE
CERTIFICATE OF CORRECTION

PATENT NO. : 5,114,741

DATED : May 19, 1992

INVENTOR(S) : Joseph J. Zupancic et al.

It is certified that error appears in the above-identified patent and that said Letters Patent is hereby corrected as shown below:

Column 4, line 34: "p" should read --P--

Column 5, line 51: "ethyl cyclopentyl" should read --ethylcyclopentyl--

Column 8, line 18: "to be maintained" should read --to be mentioned--

Columnn 11, line 22: after "temperature" insert --between about 150°C and about 200°C for 0.5-5 hours with--

Column 12, line 49: "252" should read --25°--

Column 13, line 7: "npropylbromide" should read --n-propylbromide--

Column 13, line 37: "npropylbromide" should read --n-propylbromide--

Column 14, line 14-15: "n-o propylbromide" should read --n-propylbromide--

Column 14, line 31: "Mn 520, Mw 1100" should read --Mn=520, Mw=1100--

Column 14, line 50: "icyclopentadiene" should read --dicyclopentadiene--

UNITED STATES PATENT AND TRADEMARK OFFICE
CERTIFICATE OF CORRECTION

PATENT NO. : 5,114,741

DATED : May 19, 1992

INVENTOR(S) : Joseph J. Zupancic et al.

It is certified that error appears in the above-identified patent and that said Letters Patent is hereby corrected as shown below:

Column 16, line 10: after "Thermo-O-Watch" insert --.--
Column 16, line 18: "57.0" should read --157.0--
Column 17, line 37: "4.76 g" should read --64.76 g--
Column 20, line 2: after "in which" insert --only--
Column 23, line 2: after "with toluene for" insert --1--
Column 23, line 45: "toluene for minute" should read --toluene for 1 minute--
Column 26, line 16: "$R_3 = H$" should read --$R_5 = H$--
Column 26, line 53: "R and $R_6$" should read --$R_1$ and $R_2$--

Signed and Sealed this

Fourteenth Day of September, 1993

Attest:

BRUCE LEHMAN

*Attesting Officer*  *Commissioner of Patents and Trademarks*